(12) United States Patent
Umebayashi

(10) Patent No.: US 9,320,654 B2
(45) Date of Patent: Apr. 26, 2016

(54) METHOD AND APPARATUS FOR MANUFACTURING DISPOSABLE WORN ARTICLE

(75) Inventor: Toyoshi Umebayashi, Osaka (JP)

(73) Assignee: ZUIKO CORPORATION, Osaka (JP)

(*) Notice: Subject to any disclaimer, the term of this patent is extended or adjusted under 35 U.S.C. 154(b) by 524 days.

(21) Appl. No.: 13/825,628

(22) PCT Filed: Nov. 8, 2011

(86) PCT No.: PCT/JP2011/075674
§ 371 (c)(1),
(2), (4) Date: Mar. 22, 2013

(87) PCT Pub. No.: WO2012/066974
PCT Pub. Date: May 24, 2012

(65) Prior Publication Data
US 2013/0184137 A1    Jul. 18, 2013

(30) Foreign Application Priority Data
Nov. 16, 2010  (JP) ................................ 2010-255789

(51) Int. Cl.
*A61F 13/15*     (2006.01)
*A61F 13/49*     (2006.01)
*A61F 13/56*     (2006.01)

(52) U.S. Cl.
CPC ............ *A61F 13/15* (2013.01); *A61F 13/15756* (2013.01); *A61F 13/49* (2013.01); *A61F 13/56* (2013.01)

(58) Field of Classification Search
CPC ... A61F 13/15; A61F 13/15756; A61F 13/49; A61F 13/56
USPC .......... 493/343, 344, 345, 346, 480; 156/264, 156/263, 256, 259, 517, 512
See application file for complete search history.

(56) References Cited

U.S. PATENT DOCUMENTS 5,597,437 A * 1/1997 Lange ............... A61F 13/15699
                                                     156/259
6,171,432 B1 * 1/2001 Brisebois .......... A61F 13/15699
                                                     156/260

(Continued)

FOREIGN PATENT DOCUMENTS

JP    2006-511303 A    4/2006
JP    2007-044374 A    2/2007

(Continued)

OTHER PUBLICATIONS

International Search Report for corresponding International Application No. PCT/JP2011/075674 mailed Feb. 14, 2012.

*Primary Examiner* — Hemant M Desai
*Assistant Examiner* — Valentin Neacsu
(74) *Attorney, Agent, or Firm* — Renner, Otto, Boisselle & Sklar, LLP

(57) ABSTRACT

A method for manufacturing a disposable worn article, including: severing a continuous web W along a cut-off line L1 having a predetermined wave shape, dividing the continuous web W into a first and second divided webs W1, W2; allowing the first and second divided webs W1, W2 to cross each other in a width direction X so as to reverse positions of the first and second divided webs W1, W2 in the width direction X; reversing the second divided web W2 by twisting the second divided web W2 by 180°; rotating a second side panel which is cut off from the second divided web W2 by 180°, thereby producing a second side panel PR in line symmetry with a first side panel PL which is cut off from the first divided web W1; and placing and fastening the side panels PL, PR to the side portions of the body 20.

10 Claims, 13 Drawing Sheets

(56) References Cited

U.S. PATENT DOCUMENTS

| | | | |
|---|---|---|---|
| 6,911,106 B2 * | 6/2005 | Otsubo | A61F 13/15699 156/161 |
| 6,936,129 B2 * | 8/2005 | Karami | A61F 13/15756 156/201 |
| 2001/0042584 A1 | 11/2001 | Karami et al. | |
| 2003/0074861 A1 * | 4/2003 | Thieman | B31B 19/90 53/412 |
| 2004/0122413 A1 | 6/2004 | Roessler et al. | |
| 2005/0256495 A1 * | 11/2005 | Schlinz | A61F 13/15756 604/385.201 |
| 2007/0142808 A1 | 6/2007 | Wada et al. | |
| 2008/0161766 A1 | 7/2008 | Sablone et al. | |
| 2009/0126864 A1 * | 5/2009 | Tachibana | A61F 13/15756 156/216 |
| 2010/0065199 A1 | 3/2010 | Hormung et al. | |

FOREIGN PATENT DOCUMENTS

| | | |
|---|---|---|
| JP | 2007-181543 A | 7/2007 |
| JP | 2010-514485 A | 5/2010 |
| JP | 2010-527668 A | 8/2010 |
| WO | 2005/079720 A1 | 9/2005 |

* cited by examiner

METHOD AND APPARATUS FOR MANUFACTURING DISPOSABLE WORN ARTICLE

TECHNICAL FIELD

The present invention relates to a method and an apparatus for manufacturing a disposable worn article in which side panels are fastened to an absorbent body.

BACKGROUND ART

When manufacturing disposable pants or diapers, by producing side panels, separately from an absorbent body for absorbing body fluid, and fastening them to the absorbent body, it is possible to reduce the portion to be trimmed off or to eliminate the trimming.

The lower edge of the side panel is in contact with legs, and if the lower edge is slanted diagonally, the lower edge more easily fits around the base of the legs. On the other hand, when the upper edge of the side panel is closer to being horizontal, it more easily fits around the torso of the wearer. In this case, the side panel will have a vertically asymmetric shape.

A side panel having such a vertically asymmetric shape is disclosed in the first patent document below. In a method for manufacturing a worn article of the first patent document, side panels are cut off successively from a single continuous web, and the side panels are fastened to both sides of the absorbent body.

CITATION LIST

Patent Literature

[First Patent Document] JP 2007-044374 A (Abstract)

SUMMARY OF INVENTION

With the method of the first patent document, after the side panel is fastened to a side sheet, and then the side sheet is fastened to the absorbent body. This complicates the handling of the side sheet, and it is not possible to avoid a decrease in the degree of freedom of the production line.

Therefore, it is an object of the present invention to provide a method and an apparatus for manufacturing a disposable worn article, with which it is possible to produce side panels from a continuous web in such a manner that there is little waste of material, and with which the produced side panel can be fastened to an absorbent body without fastening it to a side sheet.

A method of the present invention for achieving the object set forth above is a method for manufacturing a disposable worn article including an absorbent body, the absorbent body including a liquid-absorbing core and having a front portion covering a front surface of a torso of a wearer, a crotch portion covering a crotch of the wearer, and a back portion covering a back surface of the torso of the wearer, continuous with one another in a longitudinal direction, with first and second side panels projecting (protruding) in a girth direction perpendicular to the longitudinal direction, and the first and second side panels being fastened (attached) to a pair of side portions of the absorbent body, the method including:

a step of carrying the absorbent body along the longitudinal direction;

a step of carrying a band-shaped continuous web to be the pair of side panels along the carrying direction, the continuous web having a first side edge and a second side edge continuous in the carrying direction;

a step of severing the continuous web being carried along a virtual cut-off line having a predetermined wave shape continuous in the carrying direction of the continuous web, thereby dividing the continuous web into a first divided web having the first side edge therein and having first depressed portions and first protruding portions alternating each other along the cut-off line, and a second divided web having the second side edge therein and having second protruding portions and second depressed portions alternating each other along the cut-off line;

a first changing step of changing the carrying direction of at least one of the first divided web and the second divided web while carrying the first divided web and the second divided web so as to allow the first divided web and the second divided web to three-dimensionally cross each other in a width direction crossing the carrying direction so as to reverse positions of the first divided web and the second divided web in the width direction;

a second changing step of changing the carrying direction of at least one of the first divided web and the second divided web while carrying the divided webs so that carrying paths of the divided webs are parallel to each other;

a step of successively severing the first divided web at the first depressed portions of the first divided web, thereby successively obtaining the first side panels each having at least one of the first protruding portions and a part of the first side edge;

a reversing step of reversing (in a vertical direction) a front and a back of the second divided web;

a step of, after the reversing step, successively severing the second divided web at the second depressed portions of the second divided web, thereby successively obtaining the second side panels each having at least one of the second protruding portions and a part of the second side edge;

placing and fastening (attaching) the first side edge of each of the first side panels to one of the side portions of the absorbent body;

a rotation step of rotating each of the second side panels by 180° on a surface of the second side panels, thereby successively obtaining the second side panels in line symmetry with the first side panels; and a step of, after the rotation step, placing and fastening the second side edge of each of the second side panels to the other one of the side portions of the absorbent body.

On the other hand, an apparatus of the present invention is an apparatus for manufacturing a disposable worn article including an absorbent body, the absorbent body including a liquid-absorbing core and having a front portion covering a front surface of a torso of a wearer, a crotch portion covering a crotch of the wearer, and a back portion covering a back surface of the torso of the wearer, continuous with one another in a longitudinal direction, with first and second side panels projecting in a girth direction perpendicular to the longitudinal direction, and the first and second side panels being fastened to a pair of side portions of the absorbent body, the apparatus including:

a slitter for cutting (severing) a band-shaped continuous web to be the pair of side panels, the continuous web having a first side edge and a second side edge continuous in a carrying direction, wherein the band-shaped continuous web is severed, while being carried, along a virtual cut-off line having a predetermined wave shape continuous in the carrying direction, thereby dividing the continuous web into a first divided web having the first side edge therein and having first depressed portions and first protruding portions alternating each other along the cut-off line, and a second divided web having the second side edge therein and having second protruding portions and second depressed portions alternating each other along the cut-off line;

a plurality of rollers for guiding the first and second divided webs for changing the carrying direction of at least one of the first and second divided webs while carrying the first divided web and the second divided web so as to allow the first divided web and the second divided web to three-dimensionally cross each other in a width direction crossing the carrying direction so as to reverse positions of the first divided web and the second divided web in the width direction;

a first cutter for successively severing the first divided web at the first depressed portions of the first divided web, thereby successively producing the first side panels each having at least one of the first protruding portions and a part of the first side edge;

a reversing device for reversing a front and a back of the second divided web by twisting the second divided web by 180° about an axial line along the carrying direction;

a second cutter for successively severing the second divided web, which has been reversed, at the second depressed portions of the second divided web, thereby producing the second side panels each having at least one of the second protruding portions and a part of the second side edge;

first drum means for placing and fastening the first side edge of each of the first side panels to one of the side portions of the absorbent body; and second drum means for rotating each of the second side panels by 180° on a surface of each of the second side panels, thereby successively producing second side panels in line symmetry with the first side panels, and placing and fastening the second side edge of each of the rotated second side panels to the other one of the side portions of the absorbent body.

According to the method of the present invention, since the first and second divided webs are obtained by severing along a predetermined wave shape, the portions of the first and second side panels have shapes that are in point symmetry with each other. As the front and the back are reversed and the attitude of the second side panel, which has been cut off from the second divided web, is rotated by 180°, the second side panel, which is in point symmetry with the first side panel, now has a shape that is in line symmetry with the first side panel. By fastening (attaching) the first and second side panels, having shapes in line symmetry with each other, to the absorbent body, it is possible to manufacture worn articles without using side sheets as with conventional techniques.

Of the first and second divided webs, portions to be the first and second side panels may have shapes in point symmetry with each other, and do not need to have shapes in line symmetry with each other. Therefore, each side panel can be shaped so that the lower edge to be in contact with the leg is diagonal while the upper edge to be in contact with the torso is horizontal or close to being horizontal. Therefore, it is possible to produce a worn article having good wearability with no waste of material.

The second side panel which has been cut off is fastened (attached) to the absorbent body after being rotated by 180°, whereas the first side panel is fastened (attached) to the absorbent body after it is cut off. Therefore, the carrying distance over which each side panel which has been cut off is carried before it is fastened to the absorbent body can be made as short as possible.

DESCRIPTION OF EMBODIMENTS

Figure 1A:
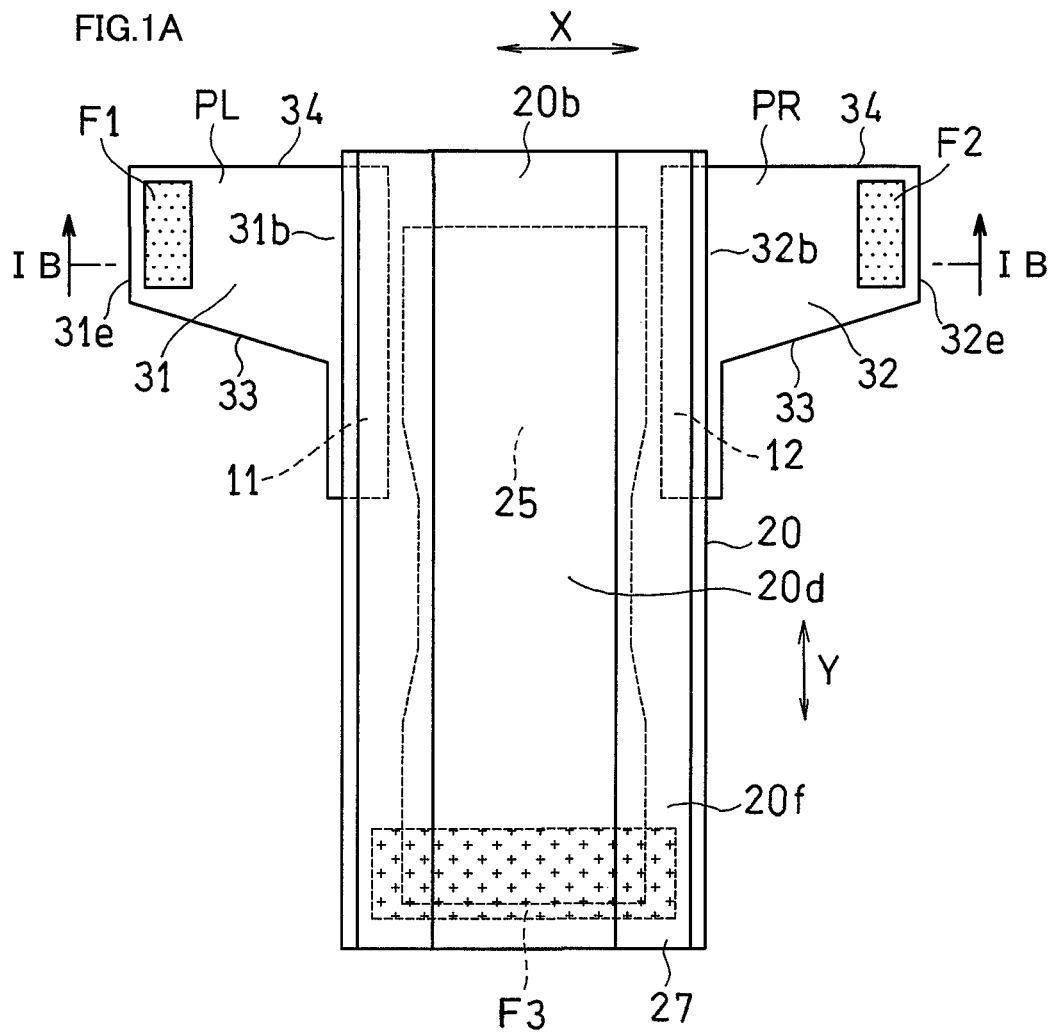
FIG. 1A is a plan view showing an example of a worn article produced by a manufacturing method of the present invention.

In a preferred embodiment of the present invention, each of the protruding portions has a lower edge extending in the girth direction and forming a part of a leg opening through which a leg of the wearer is passed, and a line of the lower edge is inclined with respect to a virtual line extending parallel to the girth direction, thereby obtaining a worn article in which the lower edge is inclined upwardly as the lower edge extends into a front portion of the torso.

In this case, the lower edge of the side panel easily fits around the leg in the leg opening (leg hole) of the worn article.

In a more preferred embodiment of the present invention, the method further includes: a step of separating adjacent ones of the first side panels from each other in the carrying direction after the first side panels are obtained and before the first side panels are fastened to the absorbent bodies; and a step of separating adjacent ones of the second side panels from each other in the carrying direction after the second side panels are obtained and before the second side panels are fastened to the absorbent bodies.

In this case, successively-produced side panels are placed at a frequency according to the length of the worn article, and fastened to the absorbent bodies.

In a more preferred embodiment of the present invention, each of the first side panels has a first projecting portion projecting in the girth direction from the first side edge, with a first fastener member to be fastened to the front portion of the absorbent body placed on the first projecting portion, and each of the second side panels has a second projecting portion projecting in the girth direction from the second side edge, with a second fastener member to be fastened to the front portion of the absorbent body placed on the second projecting portion, the method further including: a step of placing the first fastener member on a first surface of the band-shaped continuous web being carried, and the second fastener member on a second surface opposite to the first surface.

In this case, the first and second fastener members can be placed on the band-shaped continuous web, instead of severed side panels. This makes it easier to place and fasten the first and second fastener members.

In the present invention, the step of changing the carrying path may be performed before the reversing step or simultaneously with the reversing step, or may be performed after the reversing step. Moreover, the carrying direction may be changed for the first and/or second divided webs.

The positional relationship between the first divided web and the second divided web after changing the carrying direction may be any of the following.

For example, in one example, in the step of changing the carrying direction, the first and second divided webs are carried so that a relationship between the first divided web and the second divided web before the front and the back of the second divided web are reversed is such that the first protruding portion and the second protruding portion are apart from each other in the width direction, with the protruding portions located outside of the space between the first side edge and the second side edge.

In another example, in the step of changing the carrying direction, the first and second divided webs are carried so that a relationship between the first divided web and the second divided web after the front and the back of the second divided web are reversed is such that the first protruding portion and the second side edge are apart from each other in the width direction, with the first protruding portion and the second side edge located outside of the space between the second protruding portion and the first side edge.

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

Embodiments

Embodiments of the present invention will now be described with reference to the drawings.

First, prior to the description of the manufacturing method of the present invention, an example of a worn article that can be manufactured by the manufacturing method will be described.

Figure 1B:
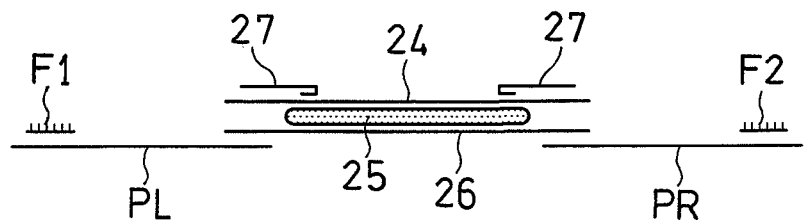
FIG. 1B is a cross-sectional view taken along line IB-IB.

FIGS. 1A and 1B show an example of a disposable diaper (an example of a worn article) according to an embodiment. FIG. 1A is a plan view showing the diaper, unfolded and stretched, and FIG. 1B is a cross-sectional view of FIG. 1A.

As shown in FIG. 1A, the present diaper includes an absorbent body 20, and a pair of side panels PL and PR fastened (attached) to the body 20.

The body 20, when worn, covers the front girth area, the crotch area and the rear girth area of the wearer. The body 20 includes a front portion 20f, a crotch portion 20d and a rear portion 20b corresponding to these areas. The front portion 20f, the crotch portion 20d and the rear portion 20b are continuous with one another in the longitudinal direction of the body 20.

The body 20 of FIG. 1B includes, for example, a pair of cuffs (anti-leak walls) 27 to be in contact with the surface of the wearer, a liquid-permeable top sheet 24, a liquid-absorbing core 25, a liquid-impermeable back sheet 26, and the like.

Note that the body 20 may include, for example, a leg elastic member (not shown). Moreover, the cuffs 27 may be omitted.

A female touch fastener F3 for receiving male touch fasteners (fastener members) F1 and F2 to be fastened thereto is provided on the non-skin-contact surface of the front portion 20f of the back sheet 26. The female touch fastener F3 is not needed if a non-woven fabric, with which the male touch fasteners F1 and F2 can engage, is used on the non-skin-contact surface of the back sheet 26.

When worn, the first and second side panels PL and PR are each located in a girth area between the front and rear portions 20f and 20b. The side panels PL and PR are, for example, fastened to the rear portion 20b so as to be projecting from left and right of the rear portion 20b of the body 20.

The side panels PL and PR may be formed by two sheet-like materials such as non-woven fabrics with an elastic member sandwiched therebetween. Under no load, the side panels PL and PR are in a shrunk state with the elastic member shrunk in the girth direction X, as shown in FIG. 1A.

Note that tab members may be fastened on the left and right of the front portion 20f of the body 20.

The first and second side panels PL and PR are fastened (attached) to the body 20 at first and second side edges 11 and 12, respectively. The first and second side panels PL and PR include first and second projecting portions 31 and 32 projecting in the girth direction X from the first and second side edges 11 and 12, respectively, and first and second male touch fasteners (fastener members) F1 and F2 are provided on the skin-contact surface of the projecting portions 31 and 32, respectively.

When worn, the side panels PL and PR are wrapped around the torso of the wearer, and the male touch fasteners F1 and F2 of the side panels PL and PR are fastened to the female touch fastener F3, thereby putting the present diaper on the wearer.

Note that instead of touch fasteners, an adhesive tape and a portion to be bonded to the adhesive tape may be provided as touch-fastening members.

The projecting portions 31 and 32 each include a lower edge 33 extending in the girth direction X and forming a part of a leg opening through which a leg of the wearer is passed, and the line of the lower edge 33 is inclined upwardly with respect to a virtual line extending horizontally in the girth direction, whereby the lower edge 33 is inclined upwardly as it extends into the front portion of the torso.

The side panels PL and PR each include an upper edge 34 opposite to the lower edge 33. The upper edge 34 has a smaller inclination than the lower edge 33 with respect to the girth direction X, and is extending generally horizontal along the girth direction X, for example.

Note that the upper edge 34 extending generally in the horizontal direction will easily fit in the girth direction X of the side panel.

The projecting portions 31 and 32 of the side panels PL and PR have a trapezoidal shape such that the height thereof gradually decreases toward projection ends 31e and 32e. The length of the first and second side edges 11 and 12 is equal to the sum of the length of the base (base ends 31b and 32b of the projecting portions 31 and 32) and the length of the upper side (the projection ends 31e and 32e) of the trapezoidal shape.

Figure 2:
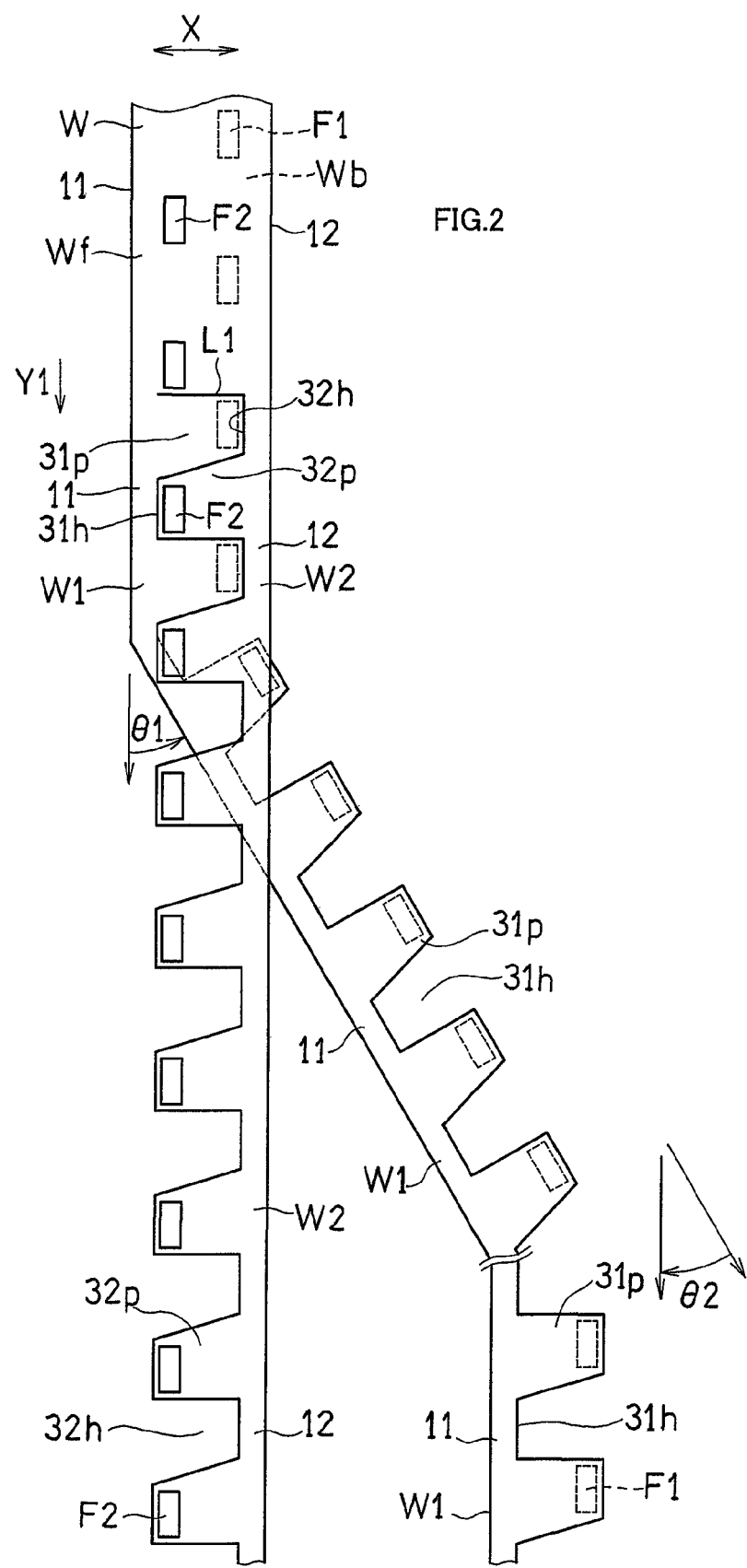
FIG. 2 is a rear view showing Embodiment 1 of a method for manufacturing a worn article of the present invention, showing a method for producing first and second divided webs.

Next, a method for manufacturing the diaper will be described. In FIG. 2, a band-shaped continuous web W includes a first side edge 11 and a second side edge 12 continuous in the carrying direction Y1, and is to be sets of the side panels PL and PR. While the band-shaped continuous web W is carried in the carrying direction Y1, the first male touch fasteners F1 are placed and bonded to the first surface (the reverse side of the drawing sheet) Wb of the continuous web W being carried, and the second male touch fasteners F2 are placed and bonded to the second surface (the front side of the drawing sheet) Wf opposite to the first surface.

After the bonding, the continuous web W, being carried, is slit along the virtual cut-off line L1 that is continuous in the carrying direction Y1 of the continuous web W and has a predetermined wave shape, thereby dividing the continuous web W into a first divided web W1 and a second divided web W2.

The first divided web W1 includes the first side edge 11 therein, and includes first depressed portions 31h and first protruding portions 31p alternating each other along the cut-off line L1. On the other hand, the second divided web W2 includes the second side edge 12 therein, and includes second protruding portions 32p and second depressed portions 32h alternating each other along cut-off line L1.

The first and second protruding portions 31p and 32p are to be the first and second projecting portions 31 and 32 (FIG. 1A), respectively. The first and second depressed portions 31h and 32h are to be leg holes of diapers.

After the slitting, the first divided web W1 and the second divided web W2 are vertically separated from each other. After the vertical separation, as shown in FIG. 2, a first changing step is performed by, while carrying the first divided web W1 and the second divided web W2, allowing the webs to three-dimensionally cross each other in the width direction X, which crosses the carrying direction Y1, and changing the carrying direction of the first divided web W1, for example, by the angle θ1 so that the positions of the first divided web W1 and the second divided web W2 in the width direction X are reversed.

After the change, a second changing step is performed by changing the carrying direction of the first divided web W1, whose carrying direction has been changed, by the angle θ2 in the opposite direction to the angle θ1, thereby making the carrying paths of the divided webs parallel to each other.

Through the first and second changing steps, the first and second divided webs W1 and W2 are carried so that the relationship between the first divided web W1 and the second divided web W2 is such that the first protruding portion 31p and the second protruding portion 32p are apart from each other in the width direction X, with the protruding portions 31P and 32P located outside of the space between the first side edge 11 and the second side edge 12. Simultaneously with the changing steps, the first divided web W1 and the second divided web W2 are separated from each other in the width direction X, and the first side edge 11 and the second side edge 12 are separated from each other so that they face each other back-to-back.

Figure 3:
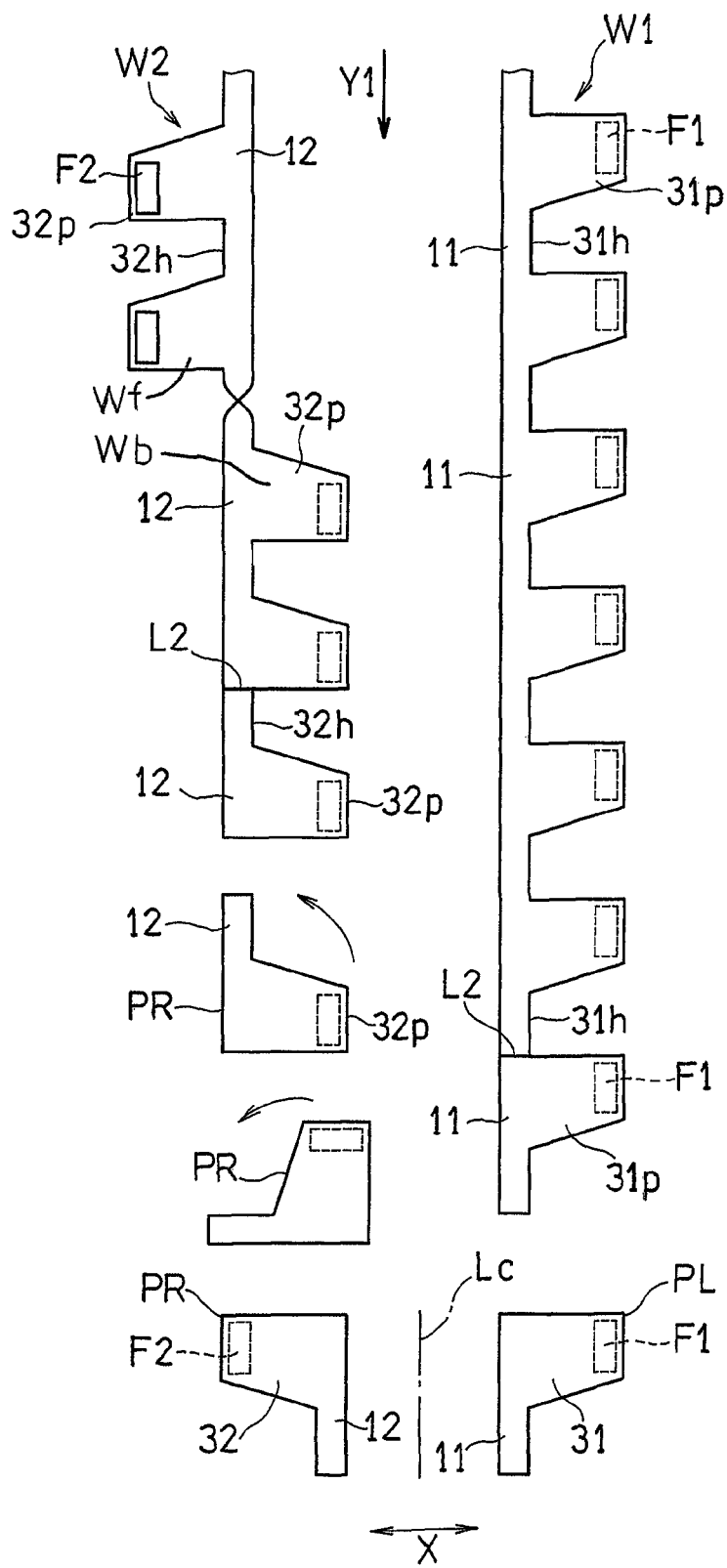
FIG. 3 is a rear view showing Embodiment 1, showing a method for producing first and second side panels.

Then, as shown in FIG. 3, a tip portion of the first divided web W1 is cut off at the first depressed portion 31h of the first divided web W1, thereby successively obtaining first side panels PL, each having the first protruding portion 31p and the first side edge 11. Immediately after the cut-off, i.e., after obtaining the first side panel PL, and before the first side panel PL is fastened to the absorbent body 20, the first side panels PL and PL are separated (spaced apart) from each other in the carrying direction.

After the separation in the width direction X, a twist step is performed, in which the front and the back of the second divided web W2 are reversed by twisting the second divided web W2 by 180° about the second side edge 12 so that the placement of the second surface Wf and the first surface Wb of the second divided web W2 is reversed. This achieves a placement in which the second protruding portion 32p of the second divided web W2 and the first side edge 11 of the first divided web W1 oppose each other.

Note that while the twist step is an example of the reversing step, it may be performed before the separation as long as it is after the slitting.

After the slitting, after the crossing step and the twist step, the tip portion of the second divided web W2 is cut off at the second depressed portion 32h of the second divided web W2, thereby successively obtaining the second side panels PR each including the second protruding portion 32p and the second side edge 12. Immediately after the cut-off, i.e., after obtaining the second side panel PR, and before the second side panel PR is fastened to the absorbent body 20, the second side panels PR and PR are separated from each other in the carrying direction.

Note that when cutting off the first and second side panels PL and PR, first and second divided webs W1 and W2 are severed along the virtual cut-off line L2 extending in the width direction X.

After the cut-off, the second side panel PR is rotated by 180° on the surface of the second side panel PR (about the virtual normal perpendicular to the first surface W1)), thereby successively obtaining second side panels PR each having a shape that is in line symmetry with the first side panel PL.

Thus, it is possible to place, on the absorbent body 20, the first and second side panels PL and PR that are in line symmetry about the center line Lc along the carrying direction.

Figure 4:
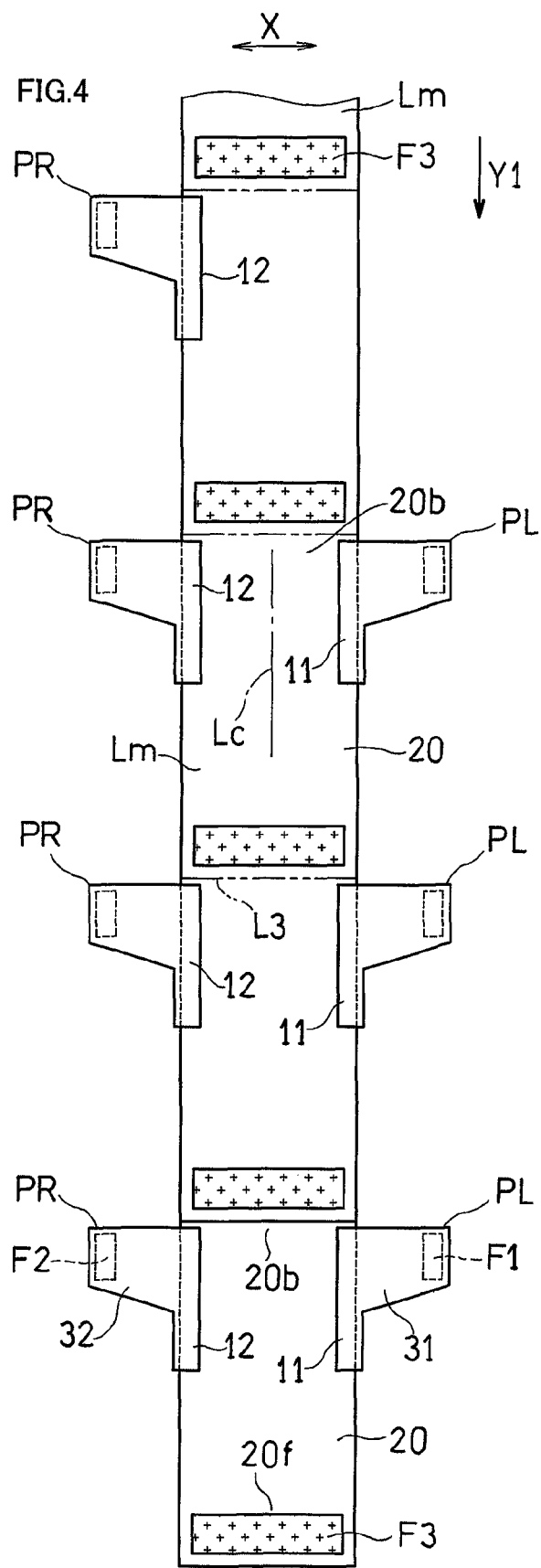
FIG. 4 is a rear view showing a method for fastening the panels to an absorbent body.

On the other hand, as shown in FIG. 4, a continuous laminate Lm to be the absorbent body 20 is carried along the carrying direction Y1. The continuous laminate Lm is a plurality of absorbent bodies 20 continuous in the carrying direction Y1. While the continuous laminate Lm is carried, the female touch fasteners F3 are placed and fastened at a predetermined frequency on the continuous laminate Lm.

Moreover, while the continuous laminate Lm is carried, the first side edge 11 of the first side panel PL is placed and fastened on (attached to) one of the side portions of the back portion 20b of the absorbent body 20. On the other hand, after the rotation step, the second side edge 12 of the second side panel PR is placed and fastened on (attached to) the other side portion of the back portion 20b of the absorbent body 20.

After the fastening, the continuous laminate Lm is severed along the virtual cut-off line L3 extending in the girth direction X, thereby obtaining individual diapers.

Next, a manufacturing apparatus for realizing the manufacturing method described above will be described.

Figure 5:
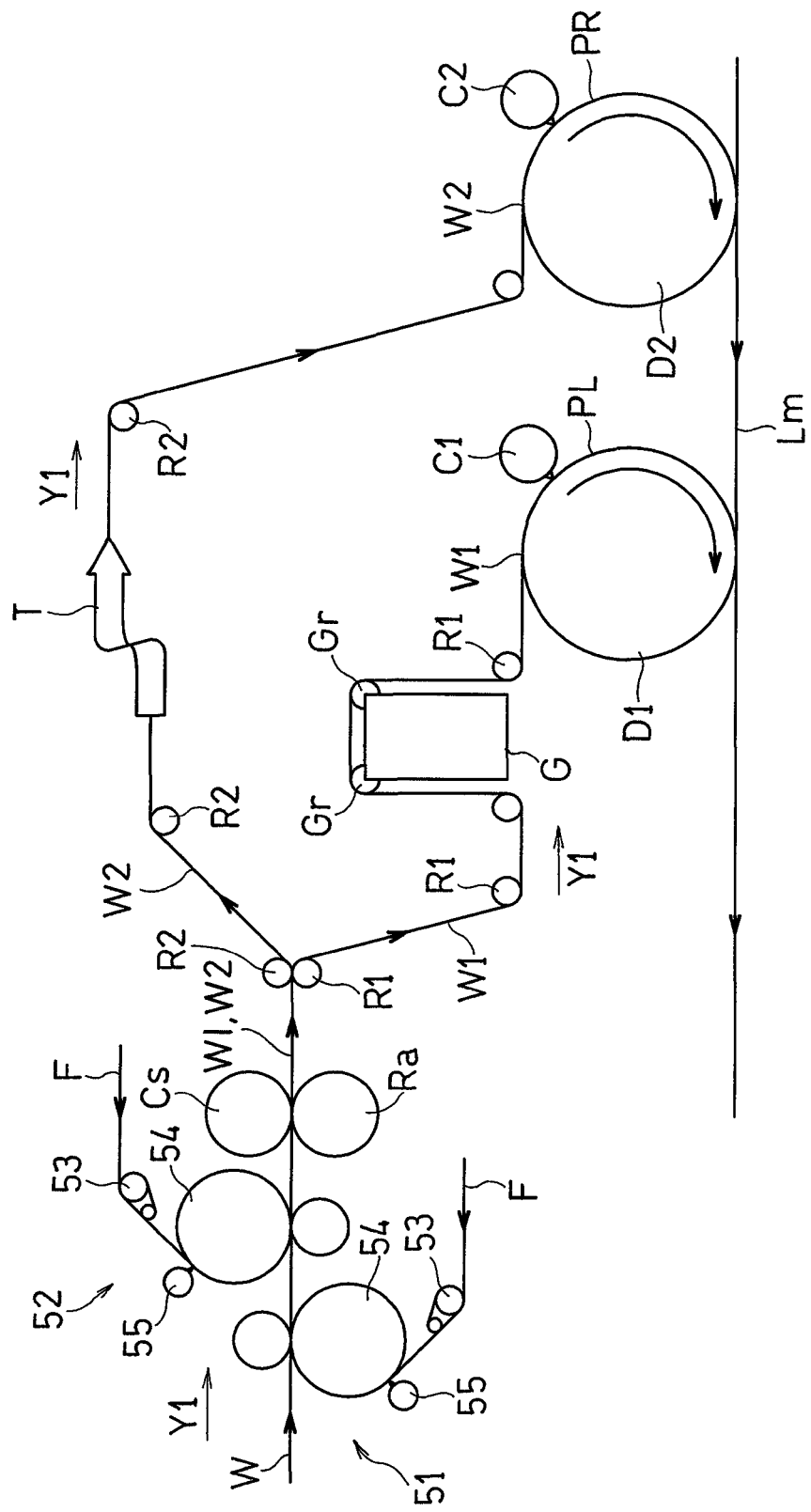
FIG. 5 is a schematic configuration view showing an embodiment of an apparatus of the present invention.

The male touch fasteners F1 and F2 of FIG. 2 are bonded on the continuous web W by fastener bonders 51 and 52 of FIG. 5. The fastener bonders 51 and 52 intermittently supply band-shaped fastener members F onto a fastener bonding roller 54 by means of a conveyer 53, and sever the fastener members F on the fastener bonding roller 54 by means of a fastener cutter 55 to a predetermined length, thereby producing the male touch fasteners F1 and F2, which are bonded on the first surface Wb and the second surface Wf of the continuous web W of FIG. 2.

The continuous web W of FIG. 2 is severed into first and second divided webs W1 and W2 by a slitter Cs and an anvil roll Ra of FIG. 5. That is, the slitter Cs includes a blade of a predetermined wave shape described above that is continuous in the carrying direction Y1, and severs the continuous web W being carried, thereby cutting the continuous web W of FIG. 2 into the first and second divided webs W1 and W2.

The first divided web W1 is carried in a diagonally downward direction by a plurality of first guide rollers R1 of FIG. 5, whereas the second divided web W2 is carried in a diagonally upward direction by a plurality of second guide rollers R2. Thus, the first divided web W1 and the second divided web W2 are vertically separated from each other.

A web guider G of FIG. 5 includes a plurality of rollers Gr, and changes the carrying direction of the first divided web W1 as shown in FIGS. 2 to 3, thereby separating the first divided web W1 and the second divided web W2 from each other in the width direction X (FIG. 3) perpendicular to the carrying direction Y1.

The first divided web W1 is severed by a first cutter C1 abutting a first drum (first drum means) D1, thereby producing first side panels PL. That is, the first cutter C1 severs the first divided web W1 at the first depressed portion 31h of the first divided web W1 of FIG. 3, thereby successively producing first side panels PL having the first protruding portion 31p and the first side edge 11.

The first drum D1 of FIG. 5 includes a plurality of first suction pads (not shown). The first suction pads are separated from one another in the circumferential direction of the first drum D1 while sucking on and carrying the first side panels PL, thereby separating the first side panels PL from one another in the carrying direction. This separation may be done by a cut-and-slip operation well known in the art.

After the separation, each first suction pad places the first side edge 11 of the first side panel PL of FIG. 4 at a position to be one side portion of the back portion of the absorbent body 20 and fastens it on the continuous laminate Lm.

The second divided web W2 heading in the upward direction on FIG. 5 is supplied to a reversing device T. The reversing device T includes a plurality of, or a large number of, well-known direction-changing rollers, and reverses the front and the back of the second divided web W2 by twisting the second divided web W2 of FIG. 3 by 180° about the second side edge 12.

The second divided web W2 of FIG. 5 is severed by a second cutter C2 abutting a second drum (second drum means) D2, thereby producing second side panels PR. That is, the second cutter C2 severs the reversed second divided web W2 of FIG. 3, thereby successively producing the second side panels PR each having the second protruding portion 32p and the second side edge 12.

The second drum D2 includes a plurality of second suction pads (not shown). The second suction pads are separated from one another in the circumferential direction of the second drum D2 while sucking on and carrying the second side panels PR, thereby separating the second side panels PR from one another in the carrying direction. Each second suction pad rotates 180° about the normal to the second drum D2 during the separation, thereby rotating the second side panel PR of FIG. 3 by 180° on the surface of the second side panel PR. Thus, the attitude of the second side panel PR is changed so that it is in a line symmetry arrangement with the first side panel PL when fastened to the absorbent body 20 of FIG. 4.

Note that the second drum D2 of FIG. 5 having the separation and rotation functions is well known in the art. The separation and the rotation may be realized by two separate drums.

After the separation and the rotation, each second suction pad places the second side edge 12 of the second side panel PR of FIG. 4 at a position to be the other side portion of the back portion of the absorbent body 20 and fastens it on the continuous laminate Lm.

Figure 6:
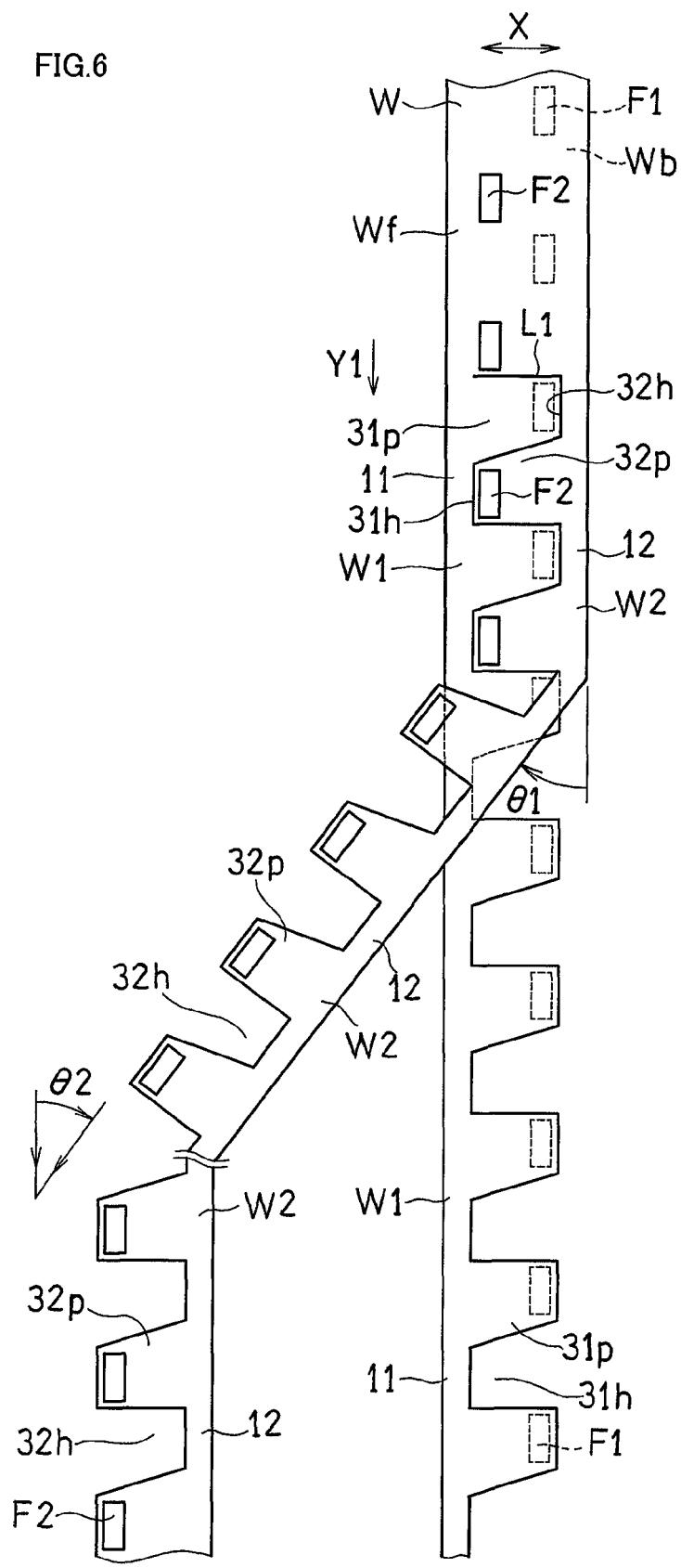
FIG. 6 is a rear view showing Embodiment 2 of a method for manufacturing a worn article of the present invention, showing a method for producing first and second divided webs.

In the manufacturing method of the present invention, the second divided web W2 and the first divided web W1 may be allowed to three-dimensionally cross each other in the width direction X by changing the carrying direction of the second divided web W2, rather than that of the first divided web W1, as shown in FIG. 6.

Figure 7:
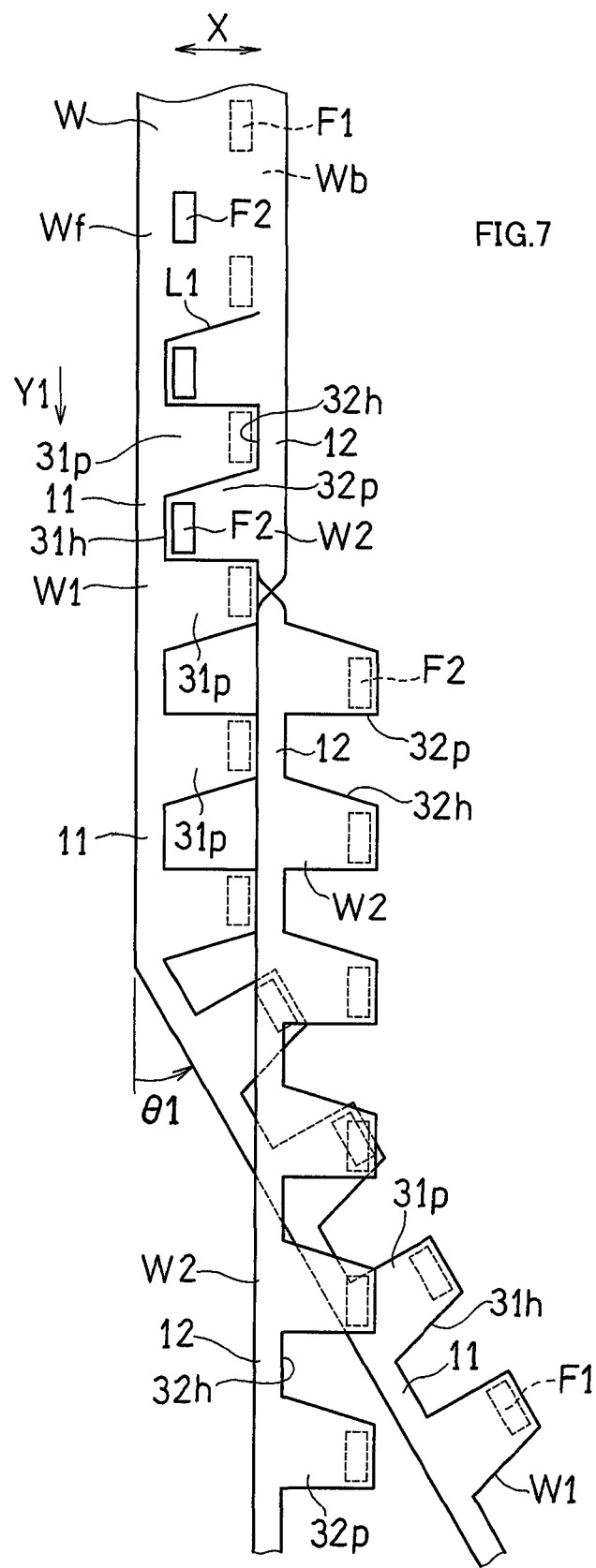
FIG. 7 is a rear view showing Embodiment 3 of a method for manufacturing a worn article of the present invention, showing a method for producing first and second divided webs.
Figure 8:
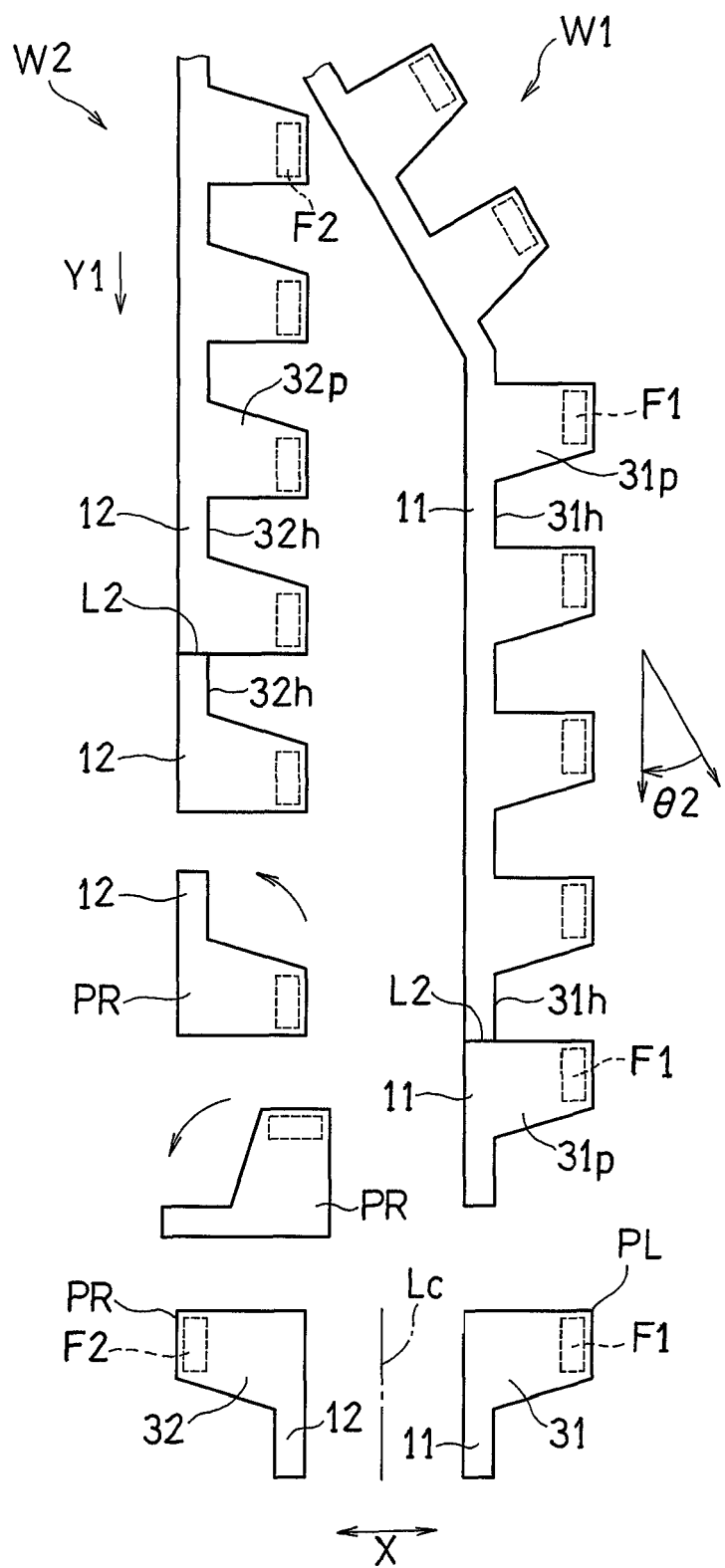
FIG. 8 is a rear view showing Embodiment 3, showing a method for producing first and second side panels.

FIGS. 7 and 8 each show a part of another example of the manufacturing method of the present invention.

In this example, before allowing the first and second divided webs W1 and W2 of FIG. 7 to three-dimensionally cross each other, the twist step of reversing the front and the back of the second divided web W2 is performed. Through this twist step, the first side edge 11 of the first divided web W1 and the second protruding portion 32p of the second divided web W2 are separated from each other, with the first side edge 11 and the second protruding portion 32p located outside of the space between the first protruding portion 31p and the second side edge 12.

After the twist step, for example, the carrying direction of the first divided web W1 is changed so as to allow the first divided web W1 and the second divided web W2 to three-dimensionally cross each other in the width direction X.

In the step of changing the carrying direction, the first and second divided webs W1 and W2 are carried so that the relationship between the first divided web W1 and the second divided web W2, of which the front and the back have been reversed, is such that the first protruding portion 31p and the second side edge 12 are apart from each other in the width direction X, with the first protruding portion 31p and the second side edge 12 located outside of the space between the second protruding portion 32p and the first side edge 11.

Note that the other steps of the present embodiment are similar to those of the example of FIGS. 2 to 4, and will not be further described below.

In the embodiment of FIGS. 2 to 8, the divided web is reversed through twisting, but the divided web does not always need to be twisted. This will be illustrated as another example of FIGS. 9 to 12.

Note that in the following example, only those steps that are different from Embodiment 1 will be mainly discussed.

Figure 9:
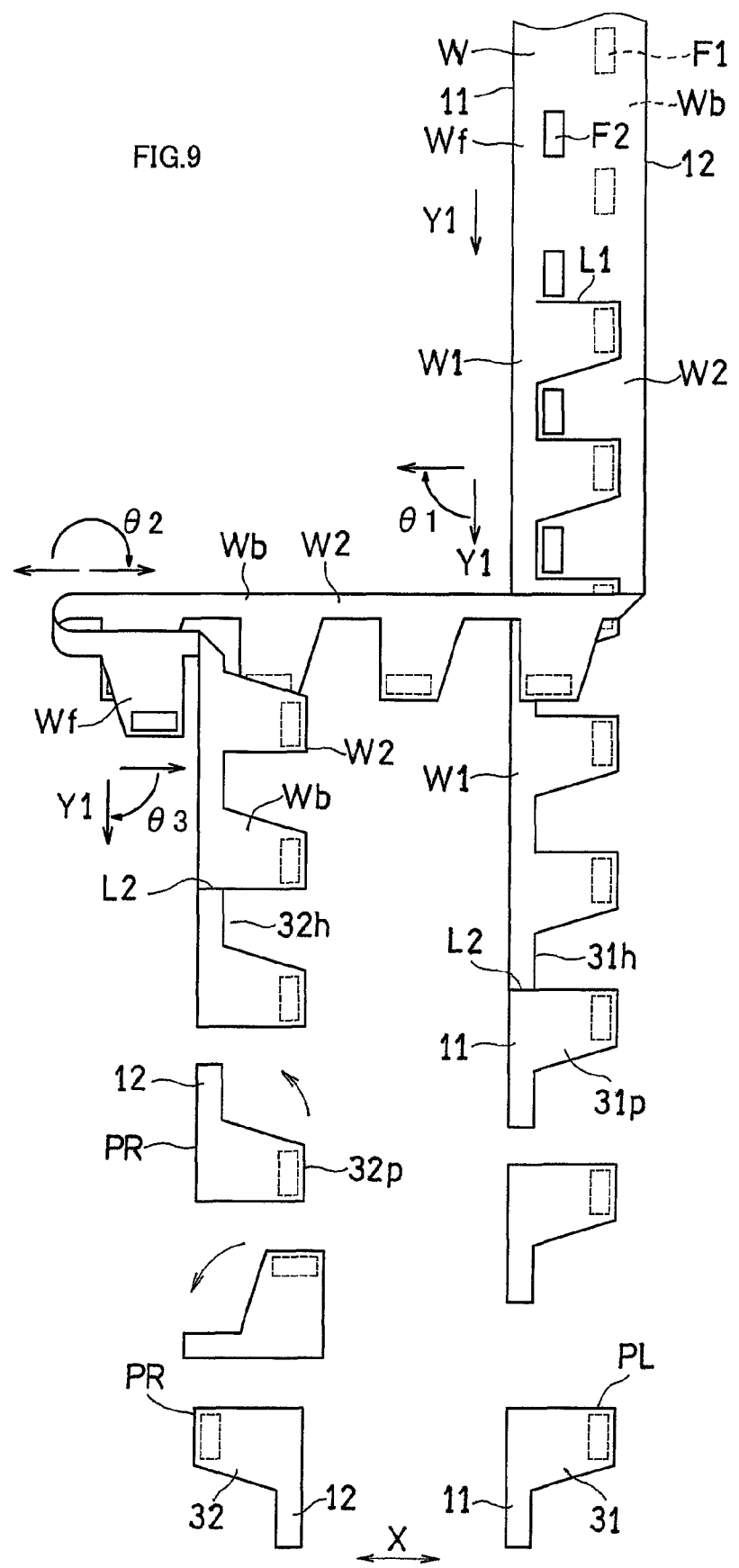
FIG. 9 is a rear view showing Embodiment 4 of a method for producing first and second side panels.
Figure 10:
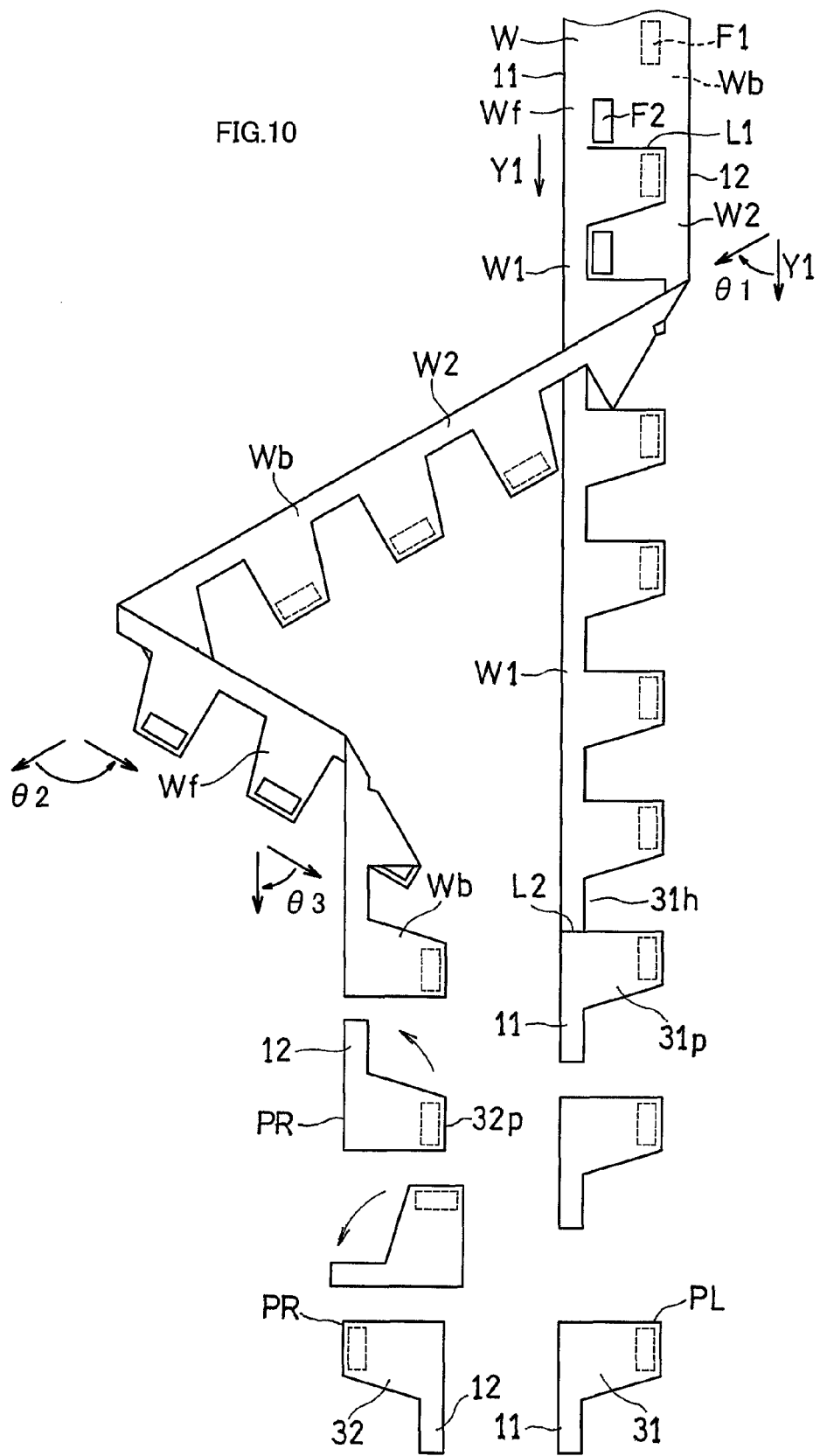
FIG. 10 is a rear view showing Embodiment 5 of a method for producing first and second side panels.

In the example of FIGS. 9 and 10, the first changing step is performed by changing the carrying direction Y1 of the second divided web W2 by the angle θ1 and reversing the second divided web W2. Then, the second divided web W2 is reversed and the carrying direction thereof is changed by the angle θ2 in the opposite direction to the angle θ1 and, moreover, the second divided web W2 is reversed and the carrying direction thereof is changed by the angle θ3 in the same direction as the angle θ1.

Note that the reversing and the change of the carrying direction of the web can be realized, for example, by well-known direction-changing rollers.

The reversing step of the second divided web W2 is realized through the three reversing operations described above.

If the value of the angle (θ1+θ2+θ3), i.e., the algebraic sum of the angles, Σθi, is set to 0°, the carrying paths of the pair of divided webs W1 and W2 are parallel to each other.

In the present invention, the first and/or second divided webs W1 and W2 may be reversed, rather than only the second divided web W2, and in a case where both of the divided webs W1 and W2 are reversed and the angles θi thereof are changed, the algebraic sum of the angles θi for one divided web can be set to 0° with respect to that for the other divided web.

Figure 11:
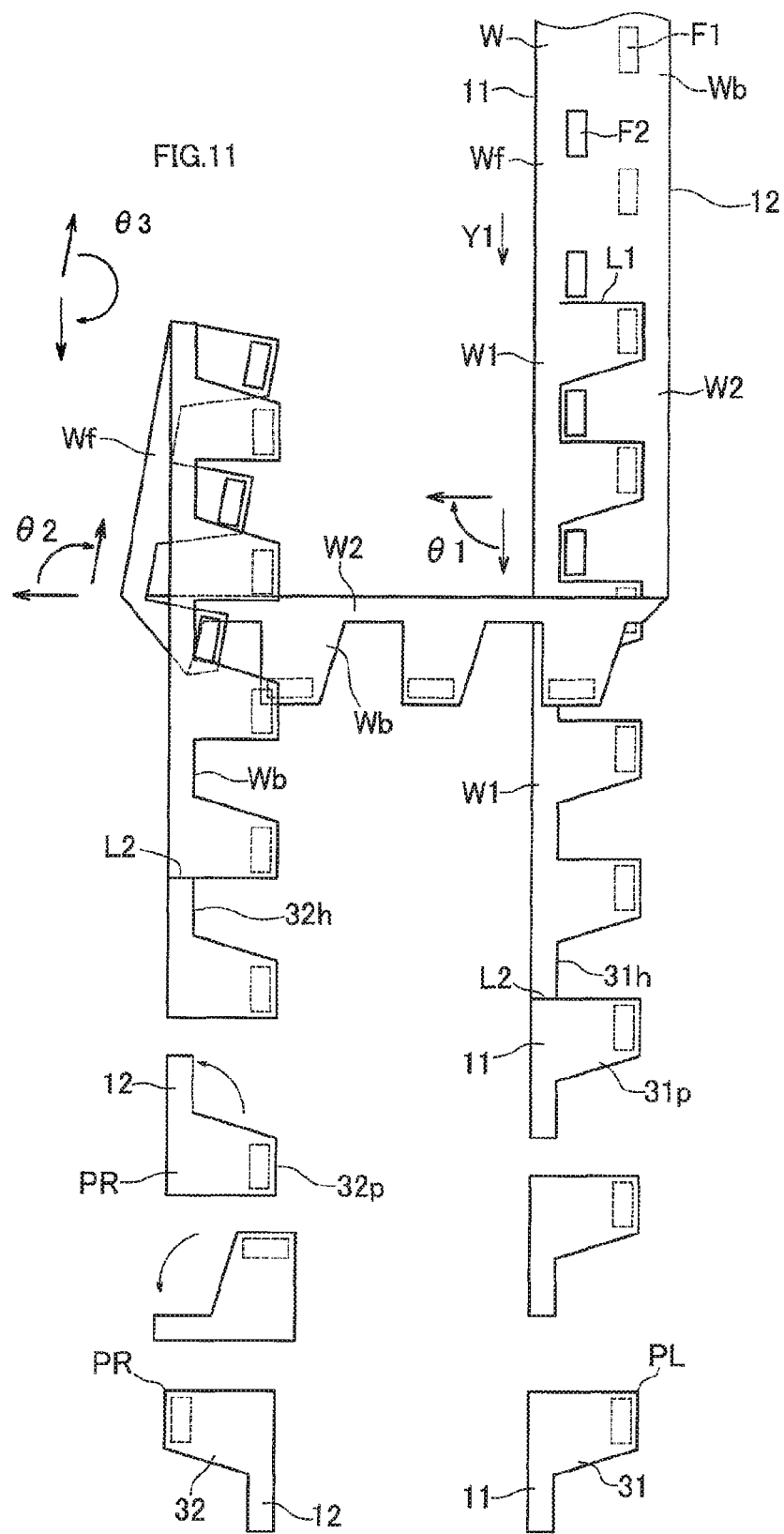
FIG. 11 is a rear view showing Embodiment 6 of a method for producing first and second side panels.

In the example of FIG. 11, the second divided web W2 is reversed three times, and the carrying direction Y1 of the second divided web W2 is changed by the angle θ1, the angle θ2 and the angle θ3 in the same direction. In this case, the carrying paths of the pair of divided webs W1 and W2 are parallel to each other if the value of the angle (θ1+θ2+θ3), i.e., the algebraic sum Σθi of the angles θi, is set to 360°.

Figure 12:
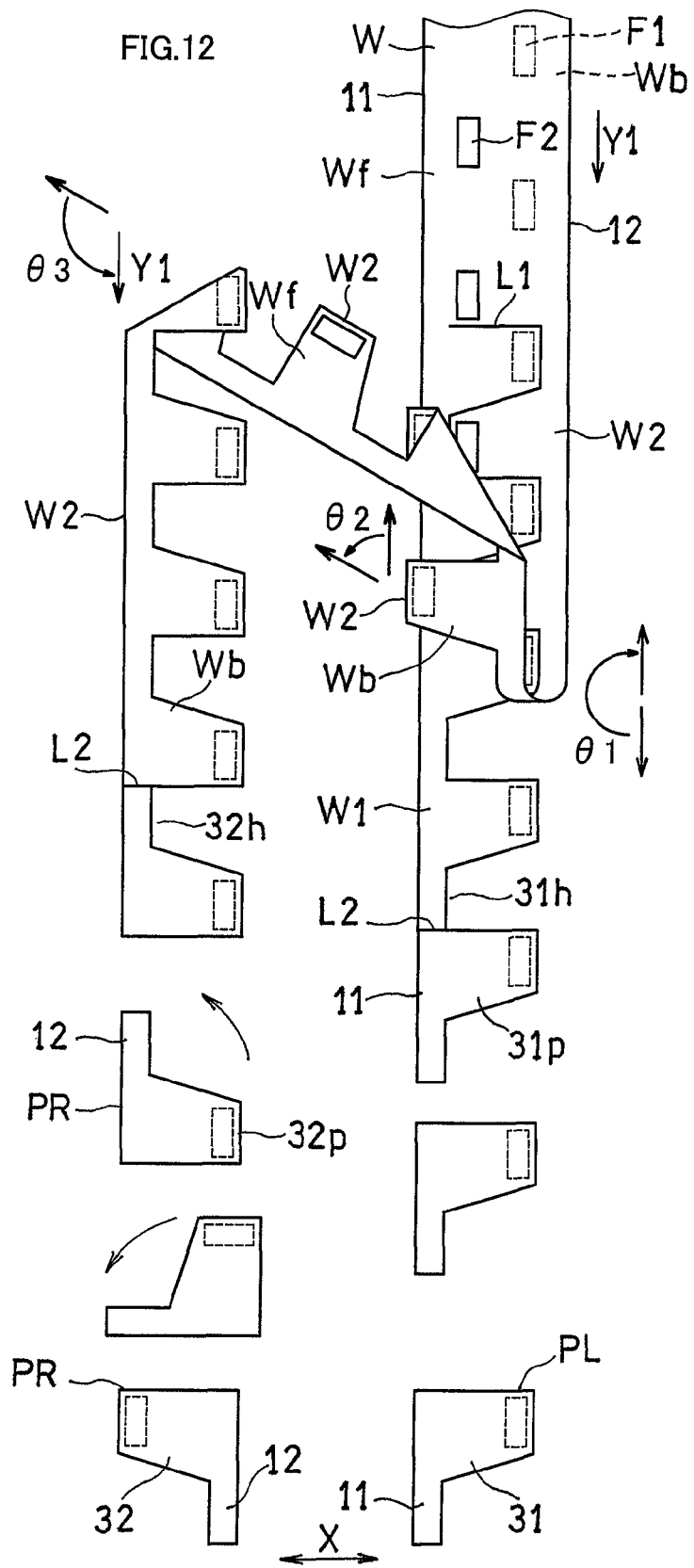
FIG. 12 is a rear view showing Embodiment 7 of a method for producing first and second side panels.

In the example of FIG. 12, after the second divided web W2 and the carrying direction thereof are reversed by 180°, the first and second changing steps are performed. In this case, Σθi is set to Σθi=0°.

Figure 13:
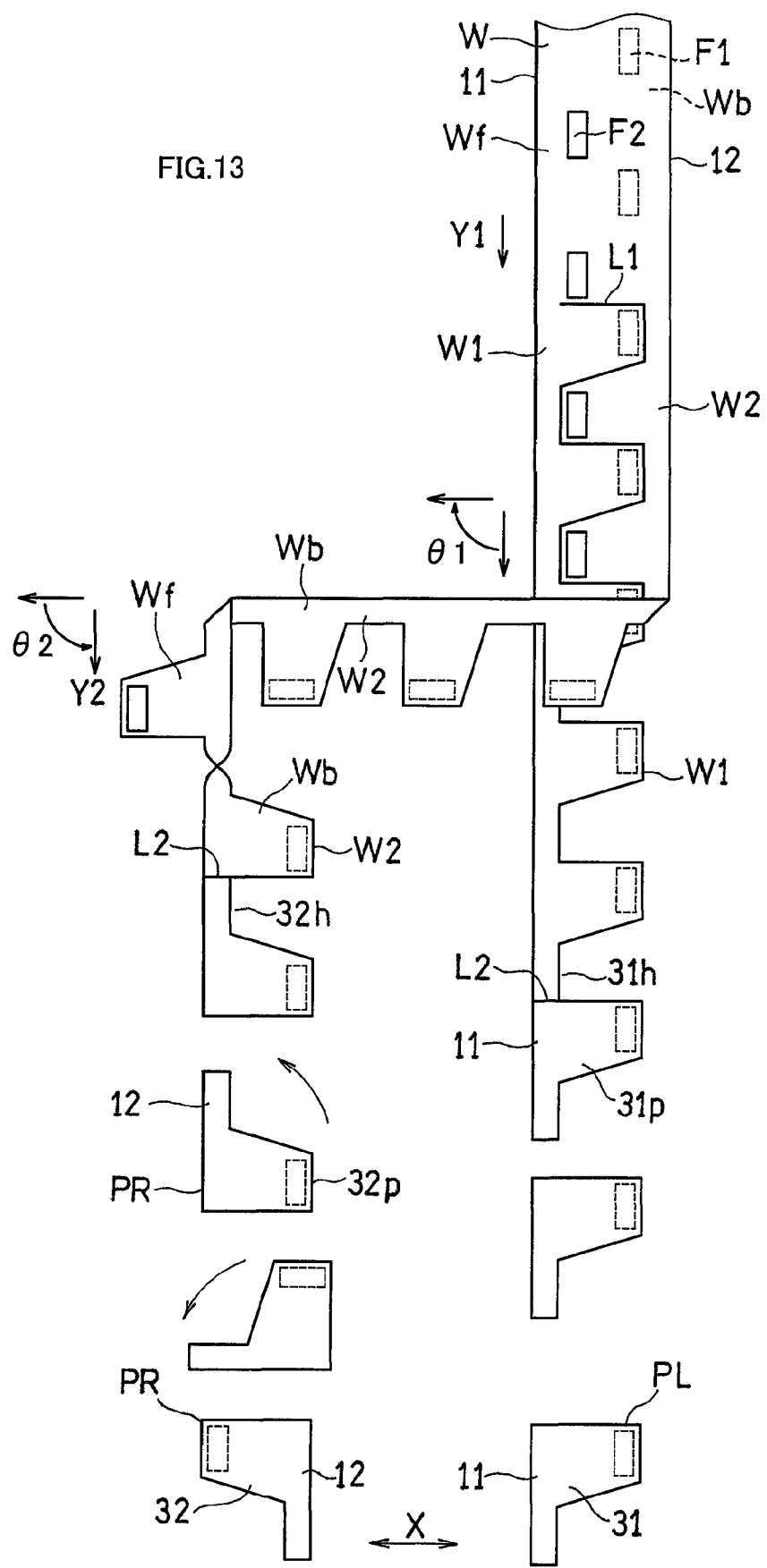
FIG. 13 is a rear view showing Embodiment 8 of a method for producing first and second side panels.

In the embodiment of FIGS. 2 to 8, the front and the back of the divided web may be reversed when changing the carrying direction of the divided web. Such an example is illustrated in FIG. 13.

As shown in this figure, in the first changing step, the front and the back of the second divided web W2 are reversed while changing the carrying direction Y1 of the second divided web W2 by the angle θ1. Then, in the second changing step, the front and the back of the second divided web W2 are reversed again while changing the carrying direction Y1 of the second divided web W2 by the same magnitude as the angle θ1 but in the opposite direction. Then, the front and the back of the second divided web W2 are reversed by twisting the second divided web W2, i.e., without changing the carrying direction Y2 of the second divided web W2.

Note that where the carrying directions of both of the divided webs W1 and W2 are changed, the carrying directions of the divided webs W1 and W2 will be parallel to each other if the algebraic sum Σθ1 of the angles θi of one divided web is 0° with respect to that of the other divided web.

While preferred embodiments have been described above with reference to the drawings, various obvious changes and modifications will readily occur to those skilled in the art upon reading the present specification.

For example, the upper edge of the side panel does not need to extend in the horizontal direction, but may extend diagonally with a smaller inclination angle than the inclination angle of the lower edge.

The first and second side panels only need to be fastened to one of the back portion and the front portion of the absorbent body. The worn article may be either a diaper or pants.

The first divided web and the second divided web may be separated from each other in the width direction, without being separated from each other vertically.

Thus, such changes and modifications are deemed to fall within the scope of the present invention, which is defined by the appended claims.

INDUSTRIAL APPLICABILITY

The present invention is applicable to disposable diapers and pants.

REFERENCE SIGNS LIST

11: First side edge, 12: Second side edge, 20: Absorbent body, 20b: Rear portion, 20d: Crotch portion, 20f: Front portion, 25: Core, 31: First projecting portion, 32: Second projecting portion, 33: Lower edge, 34: Upper edge, C1: First cutter, C2: Second cutter, D1: First drum, D2: Second drum, F1: First male touch fastener (fastener member), F2: Second male touch fastener (fastener member), G: Web guider, Lm: Continuous laminate, PL: First side panel, PR: Second side panel, W: Continuous web, W1: First divided web, W2: Second divided web, X: Girth direction (width direction), Y: Longitudinal direction, Y1: Carrying direction

The invention claimed is:

1. A method for manufacturing a disposable worn article comprising an absorbent body, the absorbent body including a liquid-absorbing core and having a front portion covering a front surface of a torso of a wearer, a crotch portion covering a crotch of the wearer, and a back portion covering a back surface of the torso of the wearer, continuous with one another in a longitudinal direction, with first and second side panels projecting in a girth direction perpendicular to the longitudinal direction, and the first and second side panels being fastened to a pair of side portions of the absorbent body, the method comprising:

a step of carrying the absorbent body along the longitudinal direction;

a step of carrying a band-shaped continuous web to become the first and second side panels along a carrying direction of the continuous web, the continuous web having a first side edge and a second side edge continuous in the carrying direction of the continuous web;

a step of severing the continuous web being carried along a virtual cut-off line having a predetermined wave shape continuous in the carrying direction of the continuous web, thereby dividing the continuous web into a first divided web being continuous along the first side edge without including the second side edge and having first depressed portions and first protruding portions alternating each other along the cut-off line, and a second divided web being continuous along the second side edge without including the first side edge and having second protruding portions and second depressed portions alternating each other along the cut-off line;

a first changing step of changing a carrying direction of at least one of the first divided web and the second divided web while carrying the first divided web and the second divided web so as to allow the first divided web and the second divided web to three-dimensionally cross each other in a width direction crossing the carrying direction of the continuous web so as to reverse positions of the first divided web and the second divided web in the width direction;

a second changing step of changing the carrying direction of at least one of the first divided web and the second divided web while carrying the divided webs so that carrying paths of the divided webs are parallel to each other;

a step of successively severing the first divided web at the first depressed portions of the first divided web, thereby successively obtaining the first side panels each having at least one of the first protruding portions and a part of the first side edge;

a reversing step of reversing a front and a back of the second divided web;

a step of, after the reversing step, successively severing the second divided web in a reversed state at the second depressed portions of the second divided web, thereby successively obtaining the second side panels each having at least one of the second protruding portions and a part of the second side edge;

a step of separating adjacent ones of the first side panels from each other in a carrying direction of the first side panels after the first side panels are obtained and before each of the first side panels is fastened to the absorbent body, a step of separating adjacent ones of the second side panels from each other in a carrying direction of the second side panels after the second side panels are obtained and before each of the second side panels is fastened to the absorbent body;

placing and fastening the first side edge of each of the first side panels to one of the pair of side portions of the absorbent body;

a rotation step of rotating each of the second side panels by 180° on a surface of each of the second side panels, thereby successively obtaining the second side panels in line symmetry with the first side panels; and a step of, after the rotation step, placing and fastening the second side edge of each of the second side panels to another one of the pair of side portions of the absorbent body.

2. The method according to claim 1, wherein each of the protruding portions has a lower edge extending in the girth direction and forming a part of a leg opening through which a leg of the wearer is passed, and a line of the lower edge is inclined with respect to a virtual line extending parallel to the girth direction, thereby obtaining a worn article in which the lower edge is inclined upwardly as the lower edge extends into a front portion of the torso.

3. The method according to claim 1, wherein each of the first side panels has a first projecting portion projecting in the girth direction from the first side edge, with a first fastener member to be fastened to the front portion of the absorbent body placed on the first projecting portion, and each of the second side panels has a second projecting portion projecting in the girth direction from the second side edge, with a second fastener member to be fastened to the front portion of the absorbent body placed on the second projecting portion, the method further comprising:

a step of placing the first fastener member on a first surface of the band-shaped continuous web being carried, and the second fastener member on a second surface opposite to the first surface.

4. The method according to claim 1, wherein:
the reversing step is executed by twisting the second divided web by 180° about an axial line along the carrying direction of the continuous web.

5. The method according to claim 4, wherein:
the first and second changing steps are executed by performing an operation of changing the carrying direction of at least one of the first divided web and the second divided web by an angle θi a plurality of times, wherein settings are such that an algebraic sum of angles θi for one of the divided webs is 0° with respect to that of the other one of the divided webs, whereby the first divided web and the second divided web are carried parallel to each other.

6. The method according to claim 1, wherein:
the reversing step is executed by performing an operation of reversing the front and the back of the second divided web one time.

7. The method according to claim 6, wherein:
the first and second changing steps are executed by performing an operation of changing the carrying direction of at least one of the first divided web and the second divided web by an angle θi a plurality of times, wherein settings are such that an algebraic sum of angles θi for one of the divided webs is 0° with respect to that of the other one of the divided webs, whereby the first divided web and the second divided web are carried parallel to each other.

8. The method according to claim 1, wherein:
in the first and second changing steps, the first and second divided webs are carried so that a relationship between the first divided web and the second divided web before the front and the back of the second divided web are reversed is such that the first protruding portions and the second protruding portions are apart from each other in the width direction, with the first and second protruding portions located outside of a space between the first side edge and the second side edge.

9. The method according to claim 1, wherein:
in the first and second changing steps, the first and second divided webs are carried so that a relationship between the first divided web and the second divided web after the front and the back of the second divided web are reversed is such that the first protruding portions and the second side edge are apart from each other in the width direction, with the first protruding portions and the second side edge located outside of a space between the second protruding portions and the first side edge.

10. An apparatus for manufacturing a disposable worn article comprising an absorbent body, the absorbent body including a liquid-absorbing core and having a front portion covering a front surface of a torso of a wearer, a crotch portion covering a crotch of the wearer, and a back portion covering a back surface of the torso of the wearer, continuous with one another in a longitudinal direction, with first and second side panels projecting in a girth direction perpendicular to the longitudinal direction, and the first and second side panels being fastened to a pair of side portions of the absorbent body, the apparatus comprising:

a slitter for cutting a band-shaped continuous web to become the first and second side panels, the continuous web having a first side edge and a second side edge continuous in a carrying direction of the continuous web, wherein the band-shaped continuous web is severed, while being carried, along a virtual cut-off line having a predetermined wave shape continuous in the carrying direction of the continuous web, thereby dividing the continuous web into a first divided web being continuous along the first side edge without including the second side edge and having first depressed portions and first protruding portions alternating each other along the cut-off line, and a second divided web being continuous along the second side edge without including the first side edge and having second protruding portions and second depressed portions alternating each other along the cut-off line;

a plurality of rollers for guiding the first and second divided webs for changing a carrying direction of at least one of the first and second divided webs while carrying the first divided web and the second divided web so as to allow the first divided web and the second divided web to three-dimensionally cross each other in a width direction crossing the carrying direction of the continuous web so as to reverse positions of the first divided web and the second divided web in the width direction;

a first cutter for successively severing the first divided web at the first depressed portions of the first divided web, thereby successively producing the first side panels each having at least one of the first protruding portions and a part of the first side edge;

a reversing device for reversing a front and a back of the second divided web by twisting the second divided web by 180° about an axial line along the carrying direction of the continuous web;

a second cutter for successively severing the second divided web in a reversed state at the second depressed portions of the second divided web, thereby producing the second side panels each having at least one of the second protruding portions and a part of the second side edge;

first drum means for placing and fastening the first side edge of each of the first side panels to one of the pair of side portions of the absorbent body after separating adjacent ones of the first side panels from each other in a carrying direction of the first side panels; and second drum means for rotating each of the second side panels by 180° on a surface of each of the second side panels while separating adjacent ones of the second side panels from each other in a carrying direction of the second side panels, thereby successively producing the second side panels in line symmetry with the first side panels, and placing and fastening the second side edge of each of the separated and rotated second side panels to another one of the pair of side portions of the absorbent body.

* * * * *